United States Patent
Kooijman

(10) Patent No.: US 9,505,690 B2
(45) Date of Patent: Nov. 29, 2016

(54) SYSTEMS AND METHODS FOR RECOVERING DIMETHYL ETHER FROM GAS MIXTURES AND LIQUID MIXTURES

(71) Applicant: SHELL OIL COMPANY, Houston, TX (US)

(72) Inventor: Hendrik Adriaan Kooijman, Amsterdam (NL)

(73) Assignee: Shell Oil Company, Houston, TX (US)

( * ) Notice: Subject to any disclaimer, the term of this patent is extended or adjusted under 35 U.S.C. 154(b) by 274 days.

(21) Appl. No.: 14/278,368

(22) Filed: May 15, 2014

(65) Prior Publication Data
US 2014/0357901 A1 Dec. 4, 2014

Related U.S. Application Data

(60) Provisional application No. 61/829,664, filed on May 31, 2013.

(51) Int. Cl.
| | |
|---|---|
| C07C 41/38 | (2006.01) |
| C07C 41/34 | (2006.01) |
| B01D 53/14 | (2006.01) |
| B01D 53/18 | (2006.01) |

(52) U.S. Cl.
CPC .......... *C07C 41/34* (2013.01); *B01D 53/1487* (2013.01); *B01D 53/18* (2013.01); *B01D 2252/103* (2013.01); *B01D 2256/24* (2013.01); *B01D 2257/704* (2013.01)

(58) Field of Classification Search
CPC ....... C07C 41/05; C07C 41/34; B01D 53/18; B01D 2256/24; B01D 2257/704
USPC ........ 568/697, 699; 585/864, 833, 836, 868; 203/95, 96; 422/260
See application file for complete search history.

(56) References Cited

U.S. PATENT DOCUMENTS

| 4,252,548 A | 2/1981 | Markbreiter et al. |
| 4,421,535 A | 12/1983 | Mehra |
| 5,037,511 A * | 8/1991 | Dornhagen ............ C07C 41/09 203/37 |
| 5,122,236 A | 6/1992 | Smith et al. |

FOREIGN PATENT DOCUMENTS

| EP | 229994 | 7/1987 |
| JP | 2004091327 | 3/2004 |

OTHER PUBLICATIONS

Martin, Pierre-Yves et al., "Liquefin: An Innovative Process to Reduce LNG Costs", 10 pages.

* cited by examiner

*Primary Examiner* — Sharon Pregler

(57) ABSTRACT

An apparatus includes an airtight shell and an absorption column arranged inside the shell. The absorption column has a multiple stage component, and a single stage component arranged below the multiple stage component with respect to gravity. A gap is arranged between the multiple stage component and the single stage component. The apparatus also includes a gas input in fluid communication with the absorption column for receiving a gas mixture, and a liquid input is in fluid communication with the absorption column for receiving a liquid mixture. A liquid-liquid separator is arranged below the absorption column with respect to gravity. The gas input is arranged below the single stage component. The liquid input is arranged above the single stage component and below the multiple stage component. A method is described for using the apparatus to remove DME from gas and liquid mixtures.

7 Claims, 3 Drawing Sheets

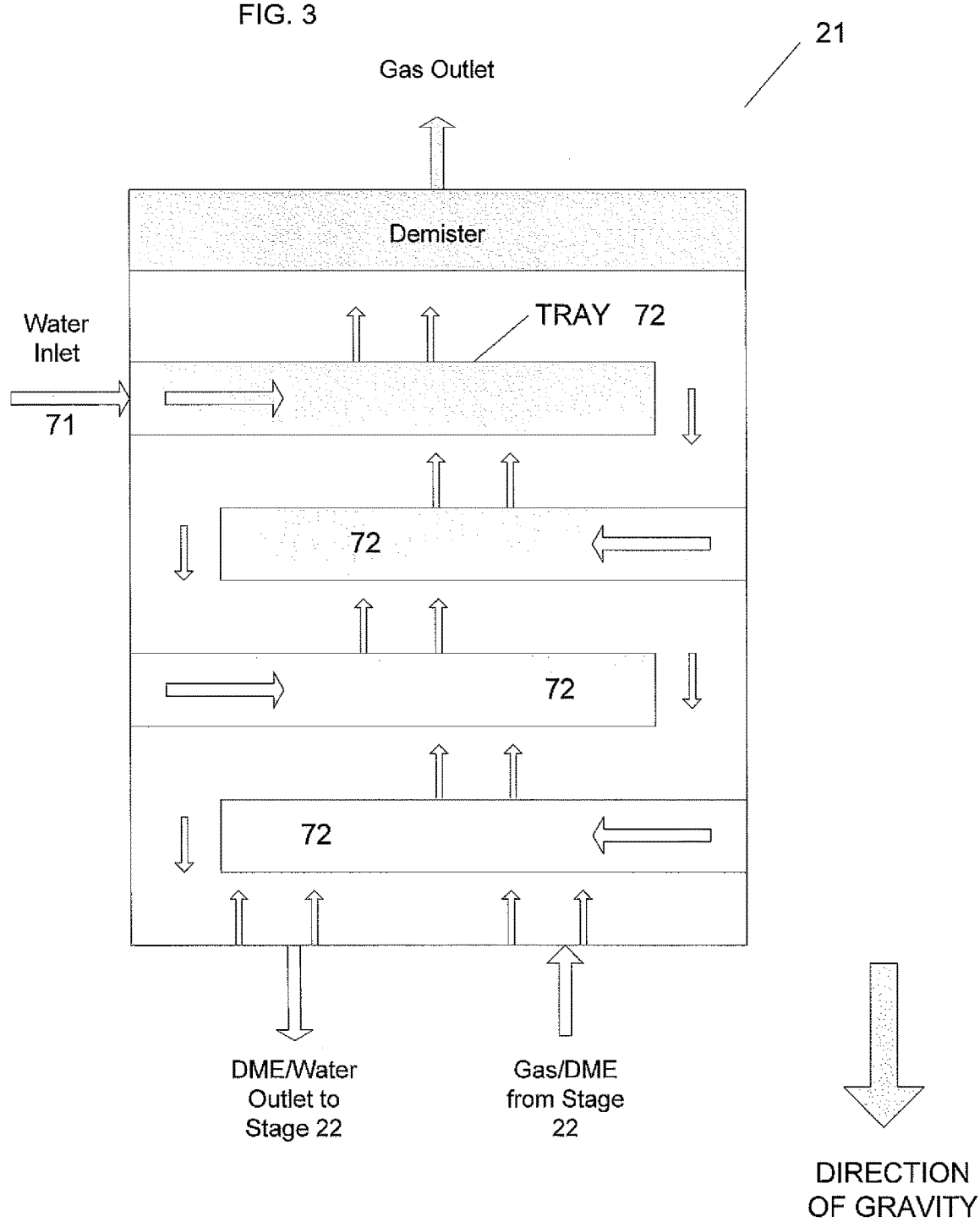

SYSTEMS AND METHODS FOR RECOVERING DIMETHYL ETHER FROM GAS MIXTURES AND LIQUID MIXTURES

PRIORITY

The present application claims the benefit of priority from U.S. patent application Ser. No. 61/829,664 filed May 31, 2014, the entire disclosure of which is hereby incorporated by reference.

FIELD OF THE INVENTION

The present disclosure is directed toward the field of dimethyl ether (DME) removal from gas and liquid phases.

BACKGROUND OF THE INVENTION

Enhanced Oil Recovery (EOR) may be used to increase oil recovery in fields worldwide beyond what can be achieved by conventional means—possibly extending the life of a field and boosting the oil recovery factor. The three main types of EOR are thermal, chemical/polymer and gas injection.

Thermal enhanced recovery works by adding heat to the reservoir. The most widely practiced form is a steam drive, which reduces oil viscosity so that it can flow to the producing wells. Chemical flooding generally reduces the capillary forces that tend to trap residual oil within the formation. Polymer flooding seals to improve the sweep efficiency of injected water. Miscible injection works in a similar way as chemical flooding. By injecting a fluid that is miscible with the oil, trapped residual oil can be recovered.

Dimethyl ether (DME) may be used for EOR as an aid for removing oil from reservoirs. However, removal of the DME from the produced oil is generally necessary before further processing. In addition, removing the DME from the produced oil can make the DME available for reinjection in a later EOR operation.

In certain methods for removing DME, such as in a water flood operation, DME is finally recovered by means of absorption from gas in water in a counter-current column operation at elevated pressures. Pressure is applied because while at low pressures DME will prefer the gas phase, but when pressures reach or exceed about 10 bar, DME will begin to partition into the hydrocarbon-rich liquid phase. However, at such increased pressures, substantial amounts of low molecular weight hydrocarbons with which DME forms azeotropes, such as propane, isobutane, n-butane and pentane may also partition into the liquid phase. Hence, direct separation with distillation is not feasible.

The conventional approach to recover DME from the hydrocarbon-rich liquid phase that forms during the compression of the produced gas is to use a one-stage or a multi-stage counter-current liquid-liquid (LL) extraction process. A common extraction solvent for counter-current liquid-liquid extraction is water. The approach uses a total draw off tray, taking the water from the wash column, running the water counter-current through an LL-extractor, and sending it to a LL separator. However, in this process, the LL-extractor generally has such a small column diameter that it is not advantageous to combine it with a gas absorption column and LL separator.

In order to overcome the above problems, the present disclosure accomplishes a recovery of DME from a hydrocarbon rich liquid phase into the water effluent of the absorption column and recycling the treated hydrocarbon back to the upstream Gas-Liquid separator to prevent relatively large losses in light hydrocarbons from the oil.

SUMMARY OF THE INVENTION

The present disclosure is directed toward the field of DME removal from gas and liquid phases.

In some embodiments of the present disclosure, recovery of DME is effected by use of an apparatus comprising an airtight shell and an absorption column arranged inside the shell. The absorption column comprises a multiple stage component, and a single stage component arranged below the multiple stage component with respect to gravity. A gap is arranged between the multiple stage component and the single stage component. The apparatus also comprises a gas input in fluid communication with the absorption column. The gas input is configured to receive a DME-containing gas mixture. A liquid input is in fluid communication with the absorption column. The liquid input is configured to receive a liquid mixture. A liquid-liquid separator is arranged below the absorption column with respect to gravity. The gas input is arranged below the single stage component with respect to gravity. The liquid input is arranged above the single stage component and below the multiple stage component with respect to gravity.

Some embodiments of the present disclosure are directed toward a method for recovering DME. The method may include the steps of supplying a gas mixture containing DME and at least one other gas to the absorption column via the gas input, supplying a liquid mixture containing DME and at least one other liquid to the single stage component of the absorption column via the liquid input, and adding water via the sprayer onto the absorption column DME is removed from the gas mixture into the water in the absorption column as the gas mixture rises upward and the water flows downward with respect to gravity. The DME is removed from the liquid mixture into the water in the single stage component as the liquid mixture and the water flow downward with respect to gravity.

In other embodiments, the method includes a step of separating the water containing the DME from the liquid mixture via the liquid-liquid separator.

Additional advantages and other features of the present disclosure will be set forth in part in the description that follows and in part will become apparent to those having ordinary skill in the art upon examination of the following or may be learned from the practice of the disclosure. The advantages of the disclosure may be realized and obtained as particularly pointed out in the appended claims. As will be realized, the present disclosure is capable of other and different embodiments, and its several details are capable of modifications in various obvious respects, all without departing from the disclosure. Accordingly, the drawings and description are to be regarded as illustrative in nature, and not as restrictive. The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combi

FIG. 3 is an illustration of a tray column absorber for use as a multiple stage component in an absorption column according to an embodiment of the present disclosure.

DETAILED DESCRIPTION OF THE INVENTION

The present disclosure is directed toward the field of DME removal from gas and liquid phases.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, and/or components, have been described at a relatively high-level, without detail, in order to avoid unnecessarily obscuring aspects of the present teachings.

Reference now is made in detail to the examples illustrated in the accompanying drawings and discussed below.

Figure 1:
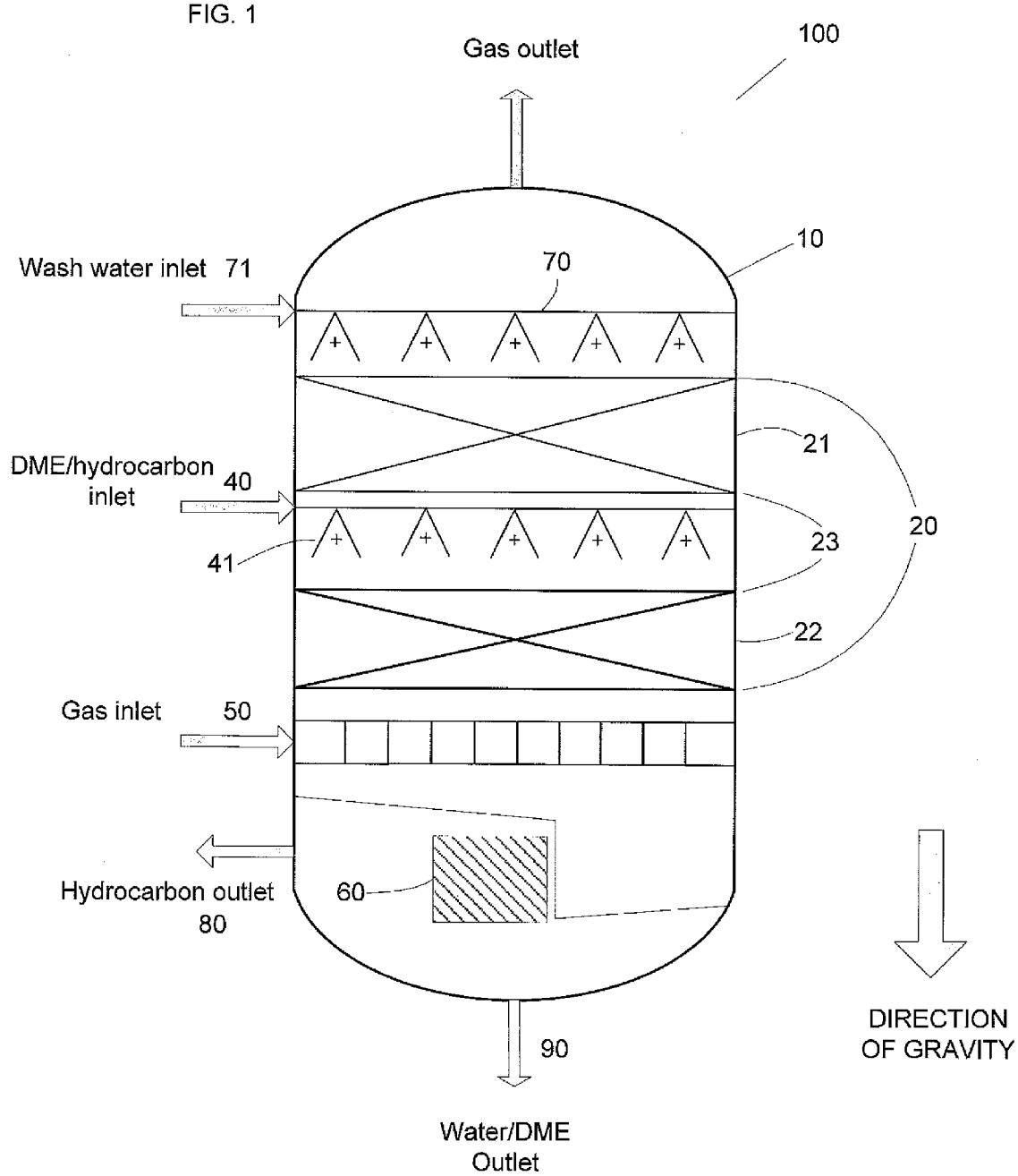
- FIG. 1 is an illustration of an apparatus for recovery of DME according to an embodiment of the present disclosure.

Referring to FIG. 1, an apparatus 100 for removing DME from a mixture includes a shell 10 for housing the various components of the apparatus 100. The shell 10 is airtight, such that pressure may be applied inside the apparatus to conduct the various DME removal operations. The shell 10 may be made of any material suitable for operations at elevated temperatures and be capable of resistance to corrosion. For example, the shell 10 may be made of passivated steel.

Within the shell 10 is an absorption column 20 for bringing compressed liquid and gas mixtures into vapor-liquid or liquid-liquid contact with an absorbent, generally water, to absorb and recover DME from a liquid or gas in the absorption column 20. The absorption column 20 is divided into a multiple stage component 21 on top and a single stage component 22 below 21. Below absorption column 20 is liquid-liquid extractor 60. The single stage component 22 and multiple stage component 21 work together to wash both DME-containing gas and DME-containing liquid hydrocarbons into a final bottoms product containing DME. That product is sent to the liquid-liquid extractor 60 where a DME-containing stream is separated into an aqueous phase and a hydrocarbon phase. As used herein, the gas phase that travels through the multiple stage component and exits at the top portion thereof is referred to as the multiple stage exit gas; the liquid phase that travels through the multiple stage component and exits at the bottom portion thereof is referred to as the multiple stage exit liquid; gas phase that travels through the single stage component and exits at the top portion thereof is referred to as the single stage exit gas; the liquid phase that travels through the single stage component and exits at the bottom portion thereof is referred to as the single stage exit liquid.

Multiple stage component 21 may be a packed column absorber, a tray column absorber, or any other known multiple stage device for contacting counter-current gas and liquid streams. FIG. 3 shows a particular embodiment of the multiple stage component 21 which uses a tray column absorber. The tray column absorber works under a similar principle as the packed column, in that gravity is used to cause a gas and a liquid to interact by flowing in opposite directions.

Whether a tray column, packed column, or some other staged system is used, the operation of multiple stage component 21 is that liquid (generally water) is injected at the top portion of the column through water inlet 71 as a gas stream containing DME rises up from below multiple stage component 21. Wash water inlet 71 is located at or near the top portion of the tray column and, in preferred embodiments, includes a distributor; that is, mechanism to evenly distribute the water across the cross section of the column, such as using sprayers 70 as shown in FIG. 1. With this arrangement, the water flows downward in a cascading fashion toward the bottom portion of the shell 10. The flow of the water is shown by down arrows. While the water flows downward, the water passes over a series of perforated trays 72. For example, four trays 72 are shown in FIG. 3, one of skill in the art will recognize that the selection of the number of trays used may vary based on separation conditions and level of DME removal desired. The level of water contained on the trays 72 may be controlled by the height of a suitable weir at the open sides of each tray 72.

During operation of the tray column shown in FIG. 3, a gas is also introduced at the bottom portion of single stage component 22, just above the liquid-liquid extractor. The gas travels up through single stage component 22 into multiple stage component 21 for further contact with an absorbent (water). In this embodiment, the gas is a mixture of DME and light hydrocarbons. In multiple stage component 21, simultaneously with the downward flow of the water, the gas rises upward through the tray column via the perforations in the trays 72 such that the gas comes into contact with the water flowing over the trays 72. This interaction between the gas and the water allows for the water to remove water soluble compounds, including DME, contained in the gas. Once extracted, the DME that was dissolved in the gas is carried downward towards the bottom portion of multiple stage component 21 in the water where it is sent to single stage component 22.

Figure 2:
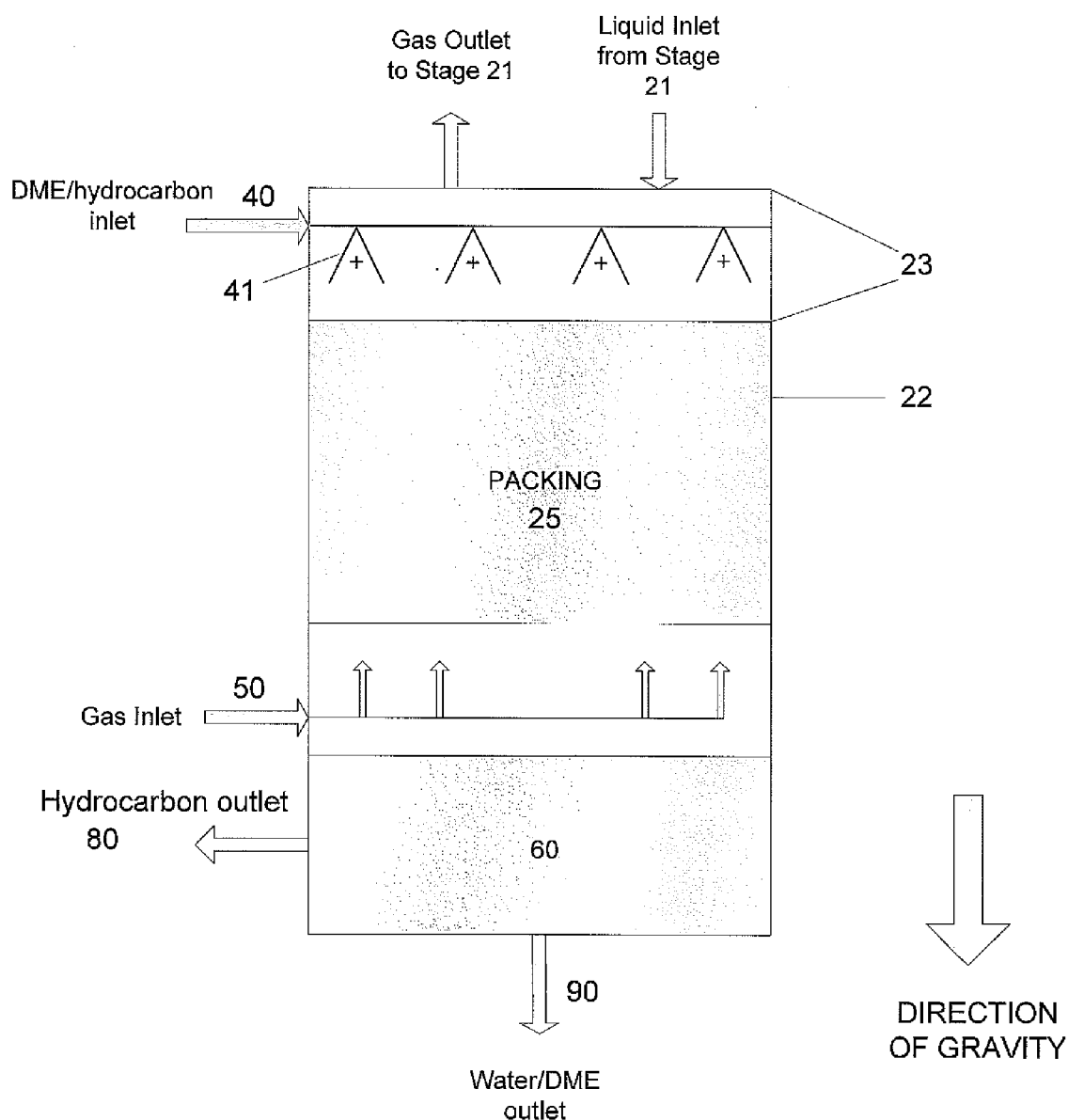
FIG. 2 is an illustration of a packed column absorber for use as a single stage component in an absorption column according to an embodiment of the present disclosure.

Referring to FIG. 1, between the multiple stage component 21 and the single stage component 22 is gap 23. The gap 23 contains a space between the multiple stage component 21 and the single stage component 22 for providing a DME/hydrocarbon inlet 40 for introduction of a liquid, such as a mixture of DME and hydrocarbons. The DME/hydrocarbon inlet 40 is introduced into the apparatus 100 via an opening in the shell 10. In preferred embodiments, the inlet is attached to a distributor; that is, a mechanism to evenly distribute the DME/hydrocarbon inlet across the cross section of the column, such as using sprayers 41 or another known injection device for introducing the DME/hydrocarbon liquid mixture to the top portion of single stage component 22. Single stage component 22 may be a packed column absorber (such as shown in FIG. 2), a tray column absorber, or any other known single stage device for contacting counter-current gas and liquid streams. A packed column absorber uses a packing material 25 to enable the contacting of gas and liquid to promote mass exchange. As the gas, such as a DME enriched gas, rises through the packing material 25, it comes into contact with water being fed from the top of the column and flows downward in the direction of gravity. In the embodiment shown in FIG. 2, the liquid fed from the top portion of single stage component 22 is the wash water from the multiple stage component 21 combined with the DME/hydrocarbon inlet stream 40.

In addition to the top liquid feeds, single stage component 22 receives a gas inlet 50 from the bottom portion of the single stage component. As shown in FIG. 1, gas inlet 50 is arranged in the shell 10 of the apparatus 100 such that a gas may be introduced below the absorption column 20 with respect to the direction of gravity. As a result, a gas or gas mixture supplied via the gas inlet 50 will rise upward opposite the direction of gravity and therefore interact with the absorption column 20. Just as with the liquid injections, it is desirable to provide a mechanism to ensure that the gas injection is distributed across the cross section of single stage component 22.

Referring to FIGS. 1 and 2, within single stage component 22, the gas which is introduced in the gas inlet 50 rises up through the packing material 25 toward the multiple stage component 21 while contacting the liquid flowing down through single stage component 22 from multiple stage component 21 and DME/hydrocarbon inlet 40. The packed column absorber uses gravity to promote mixing, in that the liquid flows downward with respect to the direction of gravity, and the gas flows upward opposite with respect to the direction of gravity.

The packed column may use any suitable packing material 25 for use with DME, hydrocarbons, water and gas. Generally, packing materials with high surface area allow for greater contact between liquid and gas, gas and gas, or liquid and liquid. Examples of packing materials for use in packed column include metal, plastic, ceramic, stoneware, and the like. Any shape or shapes of packing material suitable that allow or enhance contact between the gas and liquid, and that are sufficient for separation of DME from the gas mixture may be used. For example, Rasching rings, Berl saddle, Pall ring, Intalox saddle, hedgehog, and the like are suitable packing material shapes for separation of DME. The packing material may have a random or structured packing configuration.

Referring again to FIG. 1, as a result of the gas-water contact in the absorption column 20, the components of the gas that are soluble in water are partitioned into the water and carried downward to the liquid-liquid separator 60. The liquid-liquid separator separates two immiscible liquids that gather at the bottom portion of the apparatus 100 after passing through the absorption column 20. The liquids must be immiscible in order to separate. In certain embodiments of the present disclosure, the liquids may be water saturated with DME and a hydrocarbon mixture. In some embodiments, the liquid-liquid separator 60 may be a plate pack liquid-liquid separator. The liquid-liquid separator 60 separates the water/DME from the liquid hydrocarbons. The water/DME exits the apparatus 100 through the water/DME outlet 90 and the liquid hydrocarbons exit the apparatus 100 through the hydrocarbon outlet 80.

The present application is also directed to a method for removing DME from a liquid mixture and a gas mixture. As mentioned above, the method generally reuses the water used in the liquid-gas adsorption in the multiple stage component 21 for use in a liquid-liquid extraction in the single stage component 22. By this method, simultaneous use can be made of the water used in the liquid-gas adsorption, and the liquid-liquid extraction. In addition, simultaneous use can be made of the single stage component 22 for both the liquid-gas adsorption, and the liquid-liquid extraction.

Since the liquid-liquid extraction requires a DME/hydrocarbon liquid to be distributed across the column cross-sectional area, the gap 23 between the multiple stage component 21 and the single stage component 22 need not be large to perform a liquid-liquid extraction according to some embodiments of the present disclosure. As a result, there is no need for a liquid collector to be installed below the multiple stage component 22 to remove the wash water. The present application allows for a process intensification of two unit operations, and reduces the number of individual components from three to one.

As described previously, DME is present in each of the oil, gas and water phases from oil extraction operations. In one embodiment of the present disclosure, the method comprises supplying a gas mixture containing DME and at least one other gas to the absorption column 20 of the apparatus 100 of FIG. 1 via the gas input 50. The gas may be composed of low molecular weight compounds having 1-5 carbon atoms.

The method also includes a step of supplying a liquid mixture containing DME and at least one other liquid to the single stage component 22 of the absorption column 20 via the DME/hydrocarbon input 40. The hydrocarbon in the DME/hydrocarbon mixture may be liquid due to increased pressure. The hydrocarbon mixture may generally be a mixture of low molecular weight hydrocarbons. For example, the hydrocarbons may include propane, isobutane, n-butane and pentane.

Generally, water is added onto the top portion of the absorption column 20 via the sprayer 70. The water, in flowing down through the absorption column 20, which may include a multiple stage component 21 and a single stage component 22 described above, removes DME from both the gas mixture and the liquid mixture. The DME is partitioned from the gas mixture into the water in the absorption column 20 as the gas mixture rises upward and the water flows downward with respect to gravity. After the gas mixture passes above the absorption column 20 and the sprayer 70, it is removed from the apparatus 100 via a gas outlet.

In addition, DME is extracted from the liquid mixture into the water in the single stage component 22 as the liquid mixture and the water flow downward with respect to gravity. After the liquid mixture and DME saturated water pass through the bottom portion of the absorption column 20, the liquid mixture and DME/water are separated in the liquid-liquid separator 60. Following separation, the liquid portion, such as a hydrocarbon mixture, is removed from the apparatus 100 via the hydrocarbon outlet 80. The water/DME is removed from the apparatus 100 via the water/DME outlet 90.

The present disclosure can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the disclosure. However, it should be recognized that the present disclosure can be practiced without resorting to the details specifically set forth. In other instances, well known processing structures have not been described in detail, in order not to unnecessarily obscure the present disclosure.

The method may be performed at elevated pressures sufficient to allow for the liquifaction of the low molecular weight hydrocarbons. For example, some embodiments of the method of the present invention may be conducted at pressures of from about 10 to about 30 bar, whereas some embodiments may be conducted at pressures of from about 20 to about 30 bar.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A method for removing DME from a mixture using an apparatus, the apparatus comprising:
   an airtight shell;
   an absorption column arranged inside the shell, the absorption column comprising a multiple stage component, a single stage component arranged below the multiple stage component in the direction of gravity, and a gap arranged between the multiple stage component and the single stage component;
   a gas input in fluid communication with the absorption column, the gas input configured to receive a gas mixture at a bottom portion of the single stage component;
   a water input in fluid communication with the absorption column, the water input configured to deliver water to a top portion of the multiple stage component, the water input having a distributor configured to supply the water stream across a top portion of the absorption column;
   a liquid input in fluid communication with the absorption column, the liquid input configured to receive a DME-containing liquid mixture in the gap below the multiple stage component and above the single stage component; and
   a liquid-liquid separator arranged below the absorption column configured to receive a single stage exit liquid from the single stage component and to separate the single stage exit liquid into a hydrocarbon stream and an aqueous stream;
   the method comprising the steps of:
      supplying a gas mixture containing DME to the absorption column via the gas input,
      supplying a liquid mixture containing DME to the single stage component of the absorption column via the liquid input,
      supplying water via the distributor into the absorption column,
      partitioning the DME from the gas mixture containing DME into the water in the absorption column as the gas mixture rises upward through the absorption column,
      extracting the liquid containing DME into the water in the single stage component as the liquid containing DME flows downward through the absorption column,
   wherein water, the DME-containing liquid mixture and the DME-containing gas mixture contact in the single stage component such that a single stage exit gas exits at a top portion of the single stage component and enters the multiple stage component and the single stage exit liquid exits at the bottom portion of the single stage component and enters the liquid-liquid separator, and
   wherein the water contacts the single stage exit gas in the multiple stage component such that a multiple stage exit gas exits at the top portion of the multiple stage component and exits at a bottom portion of the multiple stage component and enters the single stage component.

2. The method of claim 1, further comprising the step of separating the water containing the DME from the liquid mixture via the liquid-liquid separator.

3. The method of claim 1, wherein the liquid mixture supplied to the single stage component is compressed at a pressure of from about 10 bar to about 30 bar.

4. The method of claim 1, wherein the liquid mixture supplied to the single stage component is compressed at a pressure of about 20 bar to about 30 bar.

5. The method of claim 1, wherein the multiple stage component comprises a packed column absorber, a tray column absorber, or a combination thereof.

6. The method of claim 1, wherein the single stage component comprises a packed column absorber, a tray column absorber, or a combination thereof.

7. The method of claim 1, wherein the multiple stage component comprises a tray column absorber and the single stage component comprises a packed column absorber.

* * * * *